United States Patent [19]

Malaugh et al.

[11] Patent Number: 5,514,165

[45] Date of Patent: May 7, 1996

[54] COMBINED HIGH VOLTAGE PULSED CURRENT AND NEUROMUSCULAR STIMULATION ELECTROTHERAPY DEVICE

[75] Inventors: John Malaugh, Trenton, N.J.; George Telepko, Fort Washington, Pa.

[73] Assignee: Jace Systems, Inc., Moorestown, N.J.

[21] Appl. No.: 172,691

[22] Filed: Dec. 23, 1993

[51] Int. Cl.⁶ .................................................. A61N 1/34
[52] U.S. Cl. .................................................. 607/46; 607/2
[58] Field of Search ................................ 607/46, 2, 50, 607/48, 62, 63, 64, 65, 66

[56] References Cited

U.S. PATENT DOCUMENTS

| | | | |
|---|---|---|---|
| 2,073,428 | 3/1937 | Schmid | 128/414 |
| 3,518,996 | 7/1970 | Cortina | 128/422 |
| 3,566,876 | 3/1971 | Stoft et al. | 128/421 |
| 3,989,051 | 11/1976 | Nozhnikov et al. | 128/421 |
| 4,140,133 | 2/1979 | Kastrubin et al. | 128/421 |
| 4,144,893 | 3/1979 | Hickey | 128/423 |
| 4,155,366 | 5/1979 | DiMucci | 128/421 |
| 4,177,819 | 12/1979 | Kofsky et al. | 607/62 |
| 4,289,136 | 9/1981 | Rienzo, Sr. | 128/421 |
| 4,324,253 | 4/1982 | Greene et al. | 128/421 |
| 4,372,319 | 2/1983 | Ichinomiya et al. | 607/62 |
| 4,640,286 | 2/1987 | Thomson | 128/421 |
| 4,682,601 | 7/1987 | Tagliavini | 128/422 |
| 4,926,865 | 5/1990 | Oman | 607/46 |
| 4,977,895 | 12/1990 | Tannenbaum | 128/421 |
| 4,996,987 | 3/1991 | Petrofsky | 607/46 |
| 5,065,083 | 11/1991 | Owens | 607/46 |

*Primary Examiner*—William E. Kamm
*Assistant Examiner*—Kennedy J. Schaetzle
*Attorney, Agent, or Firm*—Panitch Schwarze Jacobs & Nadel

[57] ABSTRACT

An electrotherapy stimulation unit having a high voltage pulsed current (HVPC) electrotherapy stimulation device providing short duration low amperage high voltage constant charge HVPC pulses to a patient to reduce pain, and a neuromuscular stimulation (NMS) electrotherapy device providing constant current NMS pulses to a patient to re-educate and prevent atrophy of muscle tissue. The HVPC device has a voltage source and at least one HVPC output circuit having a coil, a switching device, and a holding capacitor. When the switching device is turned on, an increasing current is drawn through the coil. When the switching device is turned off, a voltage spike results across the coil, charging the holding capacitor. Thereafter, the charge dissipates into the patient. The HVPC device senses the voltage provided by the voltage source and calculates the period of time the switching device is turned on based upon the sensed voltage and the preselected peak voltage of the voltage spike. The HVPC device provides a train of HVPC pulses, each HVPC pulse comprising first and second voltage spikes. The HVPC device detects whether a patient is properly connected to the HVPC output of the output circuit. If the second voltage spike is larger than the first by a predetermined value, a patient is not connected to the HVPC output circuit, and the output circuit is disabled.

10 Claims, 5 Drawing Sheets

COMBINED HIGH VOLTAGE PULSED CURRENT AND NEUROMUSCULAR STIMULATION ELECTROTHERAPY DEVICE

BACKGROUND OF THE INVENTION

The present invention relates to an electrotherapy device for providing controlled electrical stimulation to a patient. More particularly, the device comprises circuitry that provides high voltage pulsed current (HVPC) electrical stimulation to reduce pain, and circuitry that provides neuromuscular electrical stimulation (NMS) to re-educate muscular and neural tissues of the patient.

As is known, pain in a patient, especially pain arising from a surgical procedure, may be effectively reduced through the application of high voltage pulsed current (HVPC) electrotherapy. Typically, the therapy involves the use of a device that provides short duration low amperage high voltage constant charge pulses to preselected areas of the patient's tissues through electrical leads or electrodes. The therapy continues for a preselected period of time, and the patient is given the ability to control the peak voltage of the charges delivered so that the charges are received at a comfortable level.

As is also known, electrotherapy may be used after a surgical procedure has been performed in order to re-educate muscular and neural tissues and prevent atrophy thereof. Typically, a neuromuscular stimulator (NMS) device is provided for supplying constant current pulses to muscular and neural tissues of the patient through electrical leads or electrodes. As with the HVPC device, the patient is given the ability to control the amplitude of the current delivered to maintain a comfortable level.

However, the HVPC device and the NMS device have been previously supplied as separate units. Accordingly, a patient recovering from a surgical procedure must first be trained to use an HVPC device in order to control the pain arising from the surgical procedure, and then later must be trained to use an entirely different NMS device in order to re-educate muscle tissue and prevent atrophy. This can prove to be difficult and cumbersome, especially if the devices have disparate operating controls. Therefore, it is highly beneficial to a patient during rehabilitation to be able to use a single stimulating unit to provide both HVPC electrotherapy and NMS electrotherapy.

Previous HVPC devices have operated by allowing a regulated voltage supply to provide a predetermined current flow through a coil for a period of time, and then halting the flow of current. As is well known, a voltage spike results, and the voltage spike has a peak amplitude corresponding to the flow of current halted. However, the regulated voltage supplies used in prior art HVPC devices have relatively low power efficiency, as is known to one skilled in the art. The low power efficiency is especially problematic if the power source providing the input voltage to the voltage regulator is a battery. Consequently, it would be highly desirable to provide an HVPC electrotherapy device that does not use a voltage regulator and yet provides charges having preselected voltage peaks.

It would also be highly desirable to provide an HVPC device that can sense whether a patient is actually electrically connected to an output of the device and is receiving electrotherapy. A problem has arisen in previous HVPC devices in that a patient becomes separated from one or more of the HVPC electrodes, and the patient does not feel any stimulation. In response, the patient increases the intensity of the HVPC output. After discovering that in fact the electrode has fallen off, the patient attempts to re-attach the electrode, and receives a severe shock from the high intensity HVPC output. Thus, it would be advantageous to shut down the output of the HVPC device when the device senses that a patient is not electrically connected. Also, an HVPC device that senses whether a patient is electrically connected would have the further advantage that, if the power source powering the HVPC device is a battery, unnecessary use of a limited power supply would be reduced.

SUMMARY OF THE INVENTION

The present invention is directed to a new electrotherapy stimulation unit that has both HVPC and NMS devices that provide HVPC and NMS pulses. The present invention is also directed to an HVPC device that does not require a voltage regulator, and an HVPC device that can sense whether a patient is electrically connected to an output of the device.

Briefly stated, the HVPC electrotherapy device has a voltage source and at least one HVPC output circuit. The HVPC output circuit has a transformer, a switching device, and a holding capacitor. One side of the transformer primary is connected to one side of the voltage source, and the switching device selectively connects the other side of the transformer primary to the other side of the voltage source for a preselected period of time. The holding capacitor is operatively connected to the transformer secondary, and an HVPC output is connected across the holding capacitor for having leads electrically connected thereto for attachment to the body of the patient.

When the switching device is turned on, an increasing current is drawn through the transformer primary. When the switching device is turned off, the halted current causes a voltage spike having a preselected peak voltage across the transformer secondary, and the holding capacitor is charged by the voltage spike. Thereafter, the charge is dissipated into the body of the patient by way of the leads.

In a preferred embodiment of the present invention, the HVPC device senses the voltage provided by the voltage source. Further, the HVPC device calculates the preselected period of time the switching device is turned on based upon the sensed voltage and the preselected peak voltage of the voltage spike.

Typically, the HVPC device provides a train of HVPC pulses. Each HVPC pulse comprises first and second voltage spikes spaced by a preselected time period, and each HVPC pulse in the train occurs at a preselected frequency. In another preferred embodiment, the HVPC device has a patient detect circuit for detecting whether a patient is properly connected to the HVPC output of the output circuit. The patient detect circuit operates on the assumption that the second voltage spike has an increased peak amplitude with respect to the first voltage spike when a patient is disconnected from the HVPC output circuit.

Thus, the patient detect circuit detects first and second values corresponding to the peak amplitudes of the first and second voltage spikes in an HVPC pulse. Thereafter, a difference value corresponding to the difference between the first value and the second value is determined. Should the difference value exceed a predetermined value, the output circuit is disabled.

BRIEF DESCRIPTION OF THE DRAWINGS

The foregoing summary, as well as the following detailed description of a preferred embodiment of the invention, will be better understood when read in conjunction with the appended drawings. For the purpose of illustrating the invention, there is shown in the drawings embodiments which are presently preferred. It should be understood, however, that the invention is not limited merely to the precise arrangements and instrumentalities shown. In the drawings.

DETAILED DESCRIPTION OF PREFERRED EMBODIMENTS

Certain terminology may be used in the following description for convenience only and is not limiting. The words "right", "left", "upper" and "lower" designate directions of the drawings to which references are made. The words "inwardly" and "outwardly" are further directions toward and away from, respectively, the geometric center of the referenced element. The terminology includes words above specifically mentioned, derivatives thereof, and words of similar import.

Figure 1:
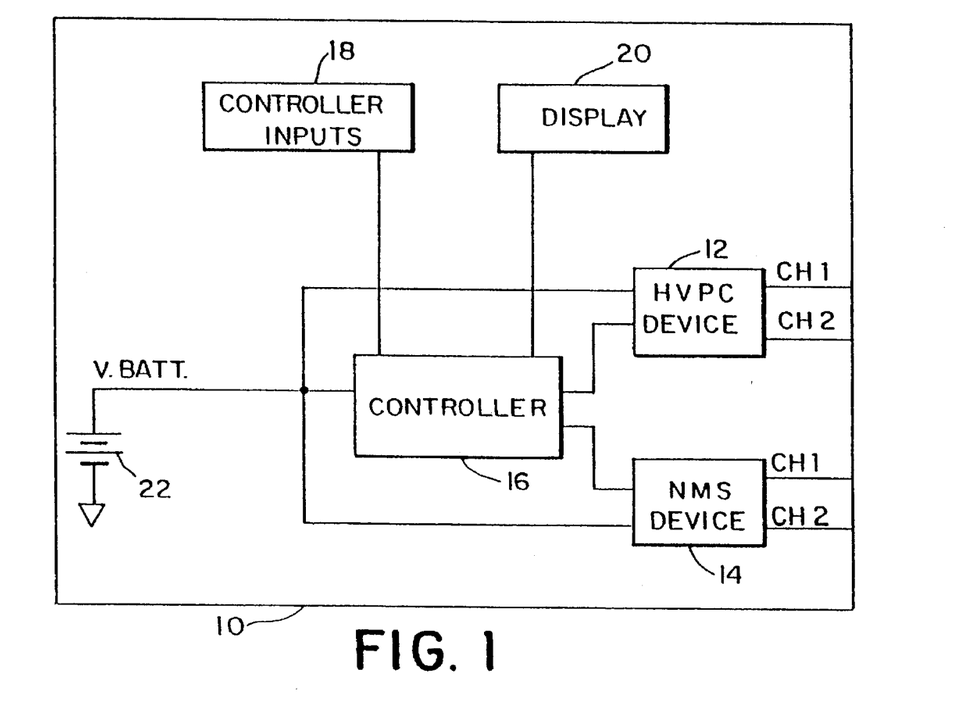
FIG. 1 is a block diagram of an electrotherapy stimulating unit having a device providing high voltage pulsed current (HVPC) charges and a device providing neuromuscular stimulation (NMS) current pulses to a patient electrically connected to the stimulator.

Referring to the drawings in detail, wherein like numerals are used to indicate like elements throughout, there is shown in FIG. 1 an electrotherapy stimulator device 10 having both a high voltage pulsed current (HVPC) device 12 and a neuromuscular stimulator (NMS) device 14 disposed therein. The electrotherapy stimulator 10 also has a controller 16 controlling both the HVPC device 12 and the NMS device 14. Preferably, the controller 16 includes a digital electronic controller having a processor, memory, multiple input and output control lines, and analog to digital converters in order to sense external voltages. Preferably, the controller 16 also includes digital to analog converters in order to provide external voltages at appropriate levels, as well as logical circuitry, buffers, and other elements necessary to interconnect the digital electronic controller to the HVPC device 12 and the NMS device 14. As one skilled in the art will recognize, the digital electronic controller may be selected from a larger variety of controllers, including an 87C552 controller, widely sold by multiple suppliers.

The controller 16 is in turn controlled by a patient and/or the patient's therapist through controller inputs 18 positioned on the electrotherapy stimulator 10. Preferably, the controller inputs 18 include operating controls and output intensity controls to allow the patient and/or the therapist to control the operation of the stimulator 10 and the intensity of the electrical stimulation. Therapist controls allow the therapist to program the operation of the stimulator 10. However, one skilled in the art will recognize that additional input controls may be useful and/or necessary for either the patient or the therapist.

Additionally, the electrotherapy stimulator 10 includes a display 20 operated by the controller 16. The display shows various parameters indicating the operation of the electrotherapy stimulator 10. As one skilled in the art will recognize, the parameters may include, but are not limited to, the mode in which the electrotherapy stimulator 10 is currently operating, the rate of stimulation, the stimulation intensity, treatment time of a particular treatment cycle, the time left for treatment in a particular cycle, and the frequency of the stimulation. Also, the display 20 may show other parameters during the programming of the electrotherapy stimulator 10 by the patient's therapist.

The electrotherapy stimulator 10 is powered by a DC power source providing a voltage $V_{BATT}$. Preferably, the power source is a standard-type 9-volt battery 22. However, one skilled in the art will recognize that different types and combinations of batteries may be used. For example, one or more 1.5 volt AA, AAA, C or D batteries may be connected in series to provide a voltage that is a multiple of 1.5 volts. Of course, one skilled in the art will also recognize that other voltage sources may be used in the present invention, including other types of batteries having the same or different voltages, an externally supplied DC voltage source, or an externally supplied AC voltage converted through an on-board converter to an appropriate DC voltage, among others.

The battery 22 provides power to the HVPC device 12, the NMS device 14, and the controller 16. The battery 22 may also supply power to the display 20 and the controller inputs 18, if necessary. It is to be understood that the controller 16 also includes circuitry for providing different preselected voltage levels derived from the battery 22 and necessary for the operation of the controller 16. For example, in a preferred embodiment the digital electronic controller as well as various other circuits require a specific voltage $V_{CC}$ in order to function.

Figure 2:
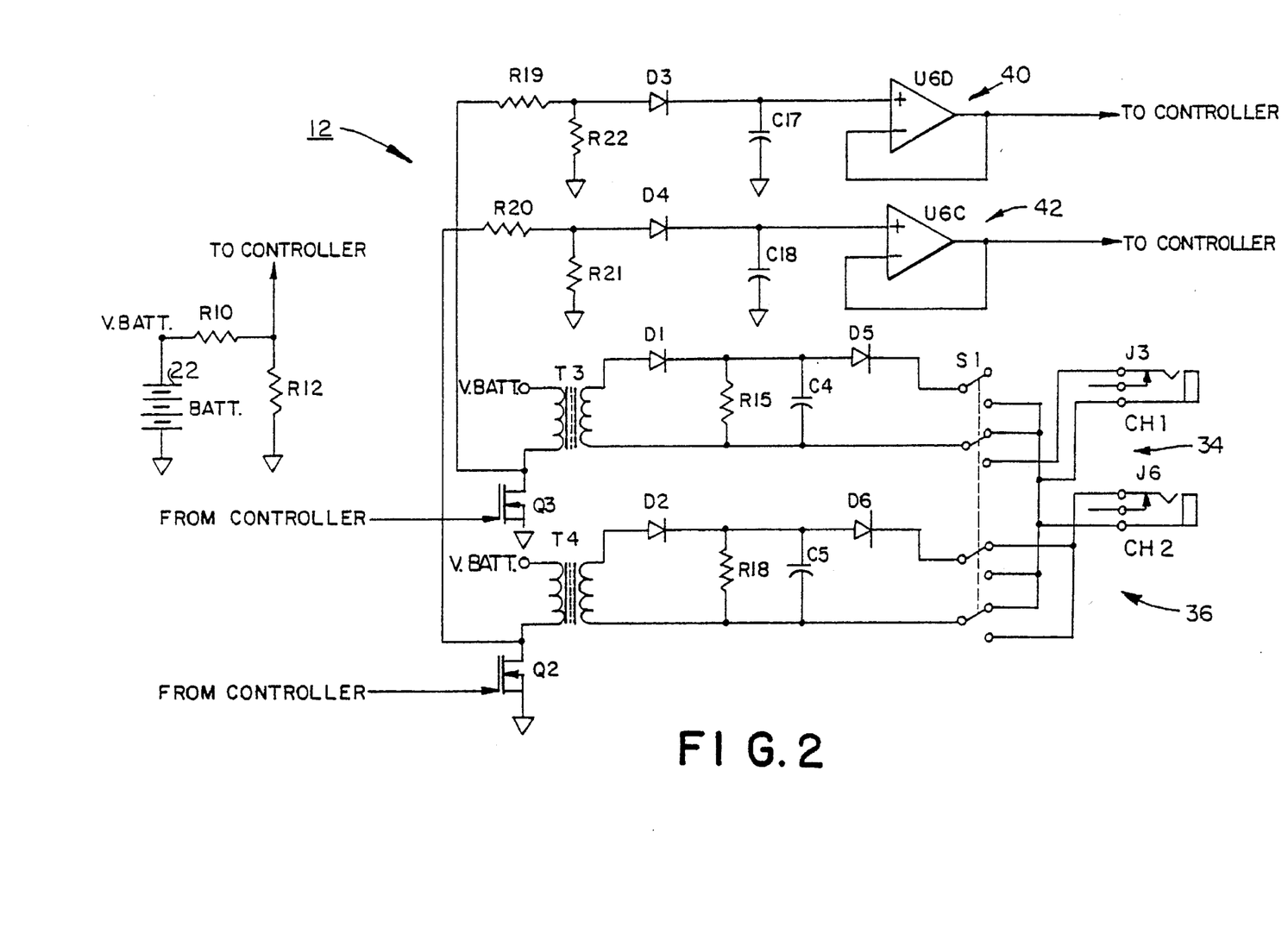
FIG. 2 is a schematic diagram of the HVPC device shown in FIG. 1, and shows two HVPC output circuits.

Referring now to FIG. 2, the high voltage pulsed current (HVPC) device 12 of the electrotherapy stimulator 10 will be described. As previously stated, the HVPC device 12 provides short duration low amperage high voltage constant charges to a patient. The HVPC device 12 has at least a first HVPC output circuit 34 providing a channel 1 output and more preferably a second HVPC output circuit 36 providing a channel 2 output. Since the first and second HVPC output circuits 34, 36 are identical, only HVPC output circuit 34 will be described.

The voltage $V_{BATT}$ from the battery 22 is applied to one contact of a primary coil. As shown in FIG. 2, the primary coil is inductively coupled to a secondary coil to form transformer T3. Preferably, transformer T3 has a turn ratio of 1:1.25 and a primary inductance of 100 μH (microhenries).

A switching transistor Q3 is interposed between the other contact of the primary coil of transformer T3 and ground. Preferably, the transistor is a junction field effect transistor, and is widely sold by multiple suppliers as part number IRF740. As is well known, the transistor has a gate, a source, and a drain. As shown in FIG. 2, the drain is electrically connected to the other contact of the primary coil of transformer T3, the source is electrically connected to ground, and the gate receives an input voltage from the controller 16. However, one skilled in the art will recognize that many other kinds of transistors and switching devices may be used in the present invention.

A holding capacitor C4 is operatively connected across the first and second contacts of the secondary coil of transformer T3, and an output jack J3 is operatively connected across the holding capacitor C4 so that electrical leads (not shown) may be inserted therein and attached to a patient. Preferably, capacitor C4 is a 400 volt 0.01 µH capacitor.

As can also be seen in FIG. 2, a first diode D1 is electrically interposed between the holding capacitor C4 and the secondary coil of the transformer T3, a second diode D5 is electrically interposed between holding capacitors C4 and the output jack J3, and a bleeder resistor R15 is electrically connected across the holding capacitor.

A quadruple pole double throw switch S1 is connected to the holding capacitor C4 of the first HVPC output circuit 34, as well as from the holding capacitor C5 of the second circuit 36. As should be apparent from FIG. 2, the switch S1 allows the patient and/or the therapist to selectively reverse the polarity of both outputs of the HVPC output circuits 34, 36. When electrical leads are appropriately attached to the output jack J3 and connected to the body of the patient, the patient forms a resistive load across the holding capacitor C4.

Figure 3A:
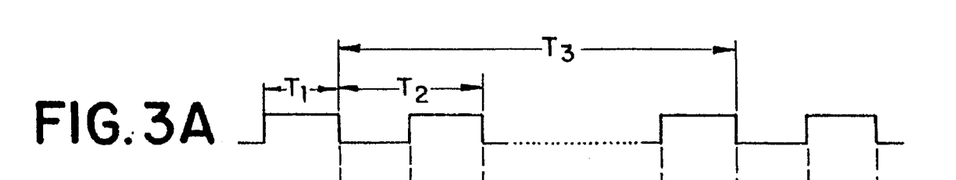
FIGS. 3A through 3D are timing diagrams showing the operation of either of the HVPC output circuits of the HVPC device shown in FIG. 2.
Figure 3B:
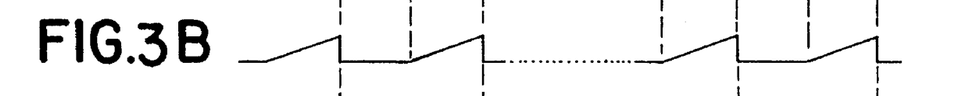
Figures 3C, 3D:
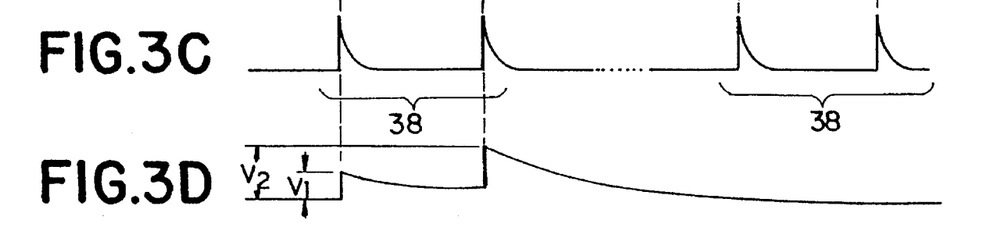

Referring now to FIGS. 3A through 3D, the operation of the HVPC output circuit 34 will be explained. FIG. 3A represents a digital signal applied by the controller 16 to the gate of transistor Q3, FIG. 3B represents the current flowing through the primary coil of the transformer T3. FIG. 3C represents the voltage across holding capacitor C4 when a patient is electrically connected to the circuit 34 and presents a resistive load (as well as a capacitive load). FIG. 3D represents the voltage across the holding capacitor C4 when a patient is not electrically connected.

When the controller 16 sets the voltage level at the gate of transistor Q3 to a high state at the beginning of a preselected time period $T_1$, as seen in FIG. 3A, the transistor Q3 is switched from a non-conductive state to a conductive state. Thus, a path is created to allow current to flow from the battery 22 through the primary coil of the transformer T3 and then to ground. Consequently, and as shown in FIG. 3B, an increasing current is drawn through the primary coil of the transformer T3. At the end of the preselected time period $T_1$, the controller 16 sets the voltage level at the gate of transistor Q3 to a low state, thus switching the transistor Q3 from the conductive state to the non-conductive state. As a result, the current path formerly created is abruptly closed down.

As a further result, and as can be seen in FIG. 3C, a voltage spike appears across both the primary and secondary coils of the transformer T3. The voltage spike across the secondary coil of the transformer T3 has a peak voltage that is a function of the current flowing through the primary coil of the transformer T3 immediately before the flow of current is halted. Preferably, the peak voltage of the voltage spike is preselected in accordance with the intensity setting selected by the patient and/or the therapist.

The voltage spike charges the holding capacitor C4, and if a patient is electrically connected to the circuit 34, the charge is then dissipated into the body of the patient by way of the leads. As seen in FIG. 3C, the resistive (and capacitive) load provided by the body of the patient combines with the capacitance of the holding capacitor C4 to produce a discharge with an exponential decay characteristic of the particular RC time constant. Typically, it is expected that the resistive load presented by the body of the patient is between 100 and 1000 ohms. Preferably, when a patient is electrically connected to the circuit 34, the holding capacitor C4 will have substantially completely discharged before the controller applies another high voltage level to the gate of the transistor Q3.

As should now be evident, the first diode D1 which is electrically interposed between the holding capacitor C4 and the secondary coil of the transformer T3 prevents the charge that is received on the holding capacitor C4 from discharging back through the secondary coil of the transformer T3. Similarly, the second diode D5 which is electrically interposed between the output and the holding capacitor C4 prevents external charges from discharging back through the HVPC output circuit 34. Lastly, the bleeder resistor R18 which is electrically connected across the holding capacitor C5 discharges the holding capacitor over a relatively long period of time if a patient is not electrically connected to the output of the HVPC output circuit 34. Preferably, the bleeder resistor R15 has a resistance significantly higher than the expected resistance of the patient, or about 200,000 ohms.

As one skilled in the art will recognize, the above-described HVPC output circuit 34 will work equally well if the transformer T3 is replaced with a single coil interposed between the battery 22 and the transistor Q3, the anode of diode D1 is electrically connected to the junction of the single coil and transistor Q3, and the capacitor C4 and resistor R15 are connected to ground (not shown). However, one skilled in the art will also recognize that in such a situation the output jacks J3 and J6 must be electrically isolated from one another.

Preferably, and as shown in FIG. 3C, the HVPC output circuit 34 is operated by the controller 16 to provide a train of HVPC pulses 38. Preferably, each HVPC pulse 38 comprises two voltage spikes spaced by a preselected time period $T_2$. Moreover, it is preferable that each of the HVPC pulses 38 is spaced by a preselected time period $T_3$ in order that each of the HVPC pulses 38 in the train occurs at a preselected frequency of $1/T_3$ pulses per second. Preferably, the preselected time period $T_2$ is about 100 microseconds and the preselected time period $T_3$ is between 10 and 1000 milliseconds, corresponding to a preselected frequency between about 1 and about 100 per second. Preferably, the preselected peak voltage of each voltage spike in each of the HVPC pulses is between about 0 and about 350 volts.

Figure 10A:
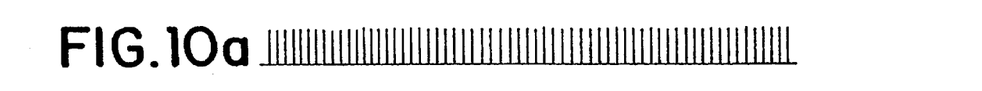
FIGS. 10a, 10b, 11a and 11b are timing diagrams showing the outputs of both output circuits in the HVPC device of FIG. 2.
Figure 10B:
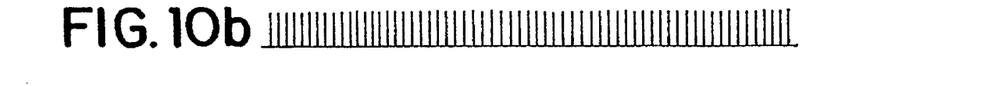
Figure 11A:
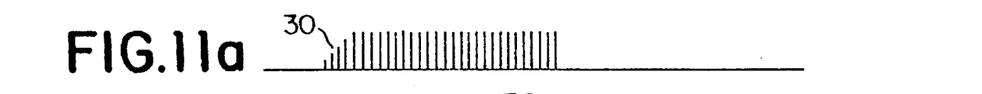
Figure 11B:
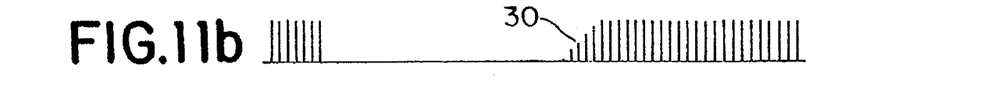

If, with respect to the HVPC device 12, FIGS. 10a and 11a represent HVPC pulses from the first HVPC output circuit 34 and FIGS. 10b and 11b represent HVPC pulses from the second HVPC output circuit 36, it is seen that the HVPC device 12 may be operated to provide trains of HVPC pulses from both circuits 34 and 36. Further, the first and second output circuits 34 and 36 are used to provide HVPC pulses to first and second areas of the tissue of the patient.

As seen in FIGS. 10a and 10b, the first and second HVPC output circuits may be operated in a simultaneous mode. In the simultaneous mode, both output circuits simultaneously provide continuous trains of HVPC pulses 38. Of course, each train initially comprises an interval (not shown) during which the intensity of each pulse increases from a minimal value to a pre-selected full value.

As seen in FIGS. 11a and 11b, the first and second HVPC output circuits may also be operated in an alternate mode. In the alternate mode, each output circuit alternately provides a train of HVPC pulses 38. Each train comprises a preselected ramp-up interval 30 during which the intensity of each pulse increases from a minimal value to a preselected full value, and each train occurs for a preselected period of time.

Since the power source for the HVPC device 12 is preferably the battery 22, provision must be made for the fact that the battery voltage $V_{BATT}$ will decrease over a period of time and with use. As previously stated, the peak voltage of the output voltage spike corresponds to the amount of current flowing to the primary coil of the transformer T3 immediately before the flow of current is halted. However, for a given period of time, the amount of such current declines in a manner corresponding to the decline of the voltage $V_{BATT}$. Accordingly, and in order to compensate, the preselected period of time $T_1$ during which current is allowed to flow must be increased.

Figure 4:
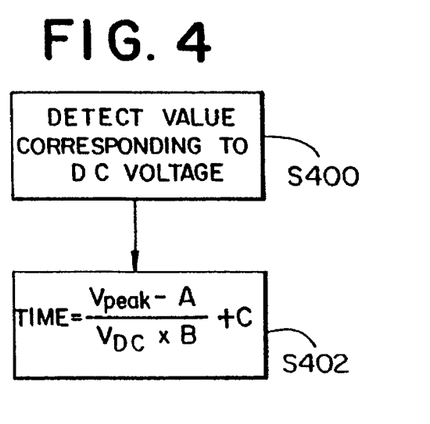
FIGS. 4 and 5 are flow charts showing the operation of the HVPC device shown in FIG. 2.

The method for calculating the time $T_1$ that the current must flow through the primary coil of the transformer T3 in order to have a voltage spike with a preselected peak voltage $V_{peak}$ will now be described with reference to FIG. 4. Preferably, and as shown in FIG. 2, a resistive divider comprising resistors R10 and R12 is attached across the battery 22 and the voltage $V_{BATT}$, and the divided voltage is input to the controller 16. Preferably, the controller 16 is able to sense and record a value $V_{DC}$ corresponding to the divided voltage. Thus, the controller 16 detects a value corresponding to the battery voltage $V_{BATT}$, as shown in step S400 of FIG. 4.

Preferably, the controller 16 includes a calculating portion able to calculate the period of time $T_1$. Through an empirical determination, it has been shown that the following equation will give the appropriate period of time $T_1$ for any given $V_{peak}$ and $V_{DC}$:

$$T_1=(V_{peak}-A)/(V_{DC}*B)+C;$$

where A, B, and C are constants that are unique to each particular kind of HVPC device. Thus, with the voltage value $V_{DC}$ and the preselected peak voltage $V_{peak}$, the controller is able to calculate the time $T_1$, as required by step S402. As a result, the predetermine peak voltage of the voltage spikes in HVPC pulses 38 is not dependent upon the voltage of the battery 22, and a voltage regulator for supplying a constant DC voltage is not necessary.

Of course, one skilled in the art will recognize that the voltage source need not necessarily be the battery 22, and that the voltage $V_{BATT}$ need not necessarily decrease over a period of time and with use. Conceivably, the voltage source could provide a voltage $V_{BATT}$ that will increase or that will increase and decrease over a period of time. Nevertheless, the method and apparatus as described above for calculating the time $T_1$ are equally applicable.

As seen in FIG. 2, the HVPC device 12 of the electrotherapy stimulator 10 also has identical patient detect circuits 40, 42, one for each of the HVPC output circuits 34 and 36. The patient detect circuits are used to determine whether a patient is electrically connected to the HVPC output circuits 34, 36. Since the circuits 40 and 42 are identical, only circuit 40 will be described. The patient detect circuit 40 measures the first and second peak amplitudes $V_1$ and $V_2$ (shown in FIG. 3D) of the first and second voltage spikes in an HVPC pulse 38 by sensing the voltage at the drain of transistor Q3. As will be recognized, the sensed voltage corresponds to the voltage across the holding capacitor C4 immediately after transistor Q3 is turned off and as a voltage spike is being produced.

In the patient detect circuit 40, the sensed voltage is divided in a resistive divider comprising resistors R19 and R22. The divided voltage is passed through a diode D3 to a peak detect capacitor C17. As should be evident, values corresponding to the peak amplitude of each voltage spike are sensed on the peak detect capacitor C17, buffered through an amplifier U6D, and then passed to the controller 16. Diode D3 prevents the peak detect capacitor C17 from discharging through resistor R22 to ground.

Figure 5:
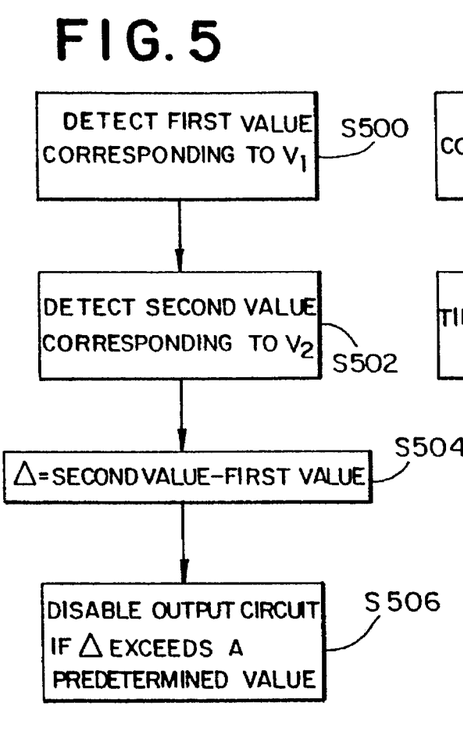

With reference to FIG. 5, the method for detecting whether a patient is electrically connected to the HVPC output circuits 34, 36 will be described. At the appropriate moments, the controller 16 detects and records first and second values corresponding to the first and second peak amplitudes $V_1$ and $V_2$, as shown at steps S500 and S502. Thereafter, and as shown at step S504, the controller 16 determines a difference value corresponding to the difference between the first value and the second value.

As seen in FIG. 3C, and as previously described, when a patient is connected to the output of the HVPC output circuit 34, the holding capacitor C4 will discharge relatively quickly to a zero or minimal voltage before the second voltage spike in an HVPC pulse 38 recharges the holding capacitor C4. However, and as seen in FIG. 3D, if a patient is disconnected from the HVPC output circuit 34, the voltage across the holding capacitor C4 does not discharge relatively quickly, and instead discharges over a long period of time through the bleeder resistor R15. Accordingly, the second voltage spike occurs and recharges the holding capacitor C4 before the holding capacitor C4 discharges to a zero or minimal voltage. As a result, the peak amplitude $V_2$ of the second voltage spike is higher than the peak amplitude $V_1$ of the first voltage spike.

Thus, and as shown at step S506, if the controller 16 determines that the difference value corresponding to the difference between the first value and the second value is greater than a predetermined value for the preselected peak voltage, the controller will then disable the HVPC output circuit 34. Preferably, the predetermined value is determined from the equation:

$$LIMIT=PEAK1/D+E;$$

wherein LIMIT is the predetermined value, PEAK1 is the first value corresponding to the first peak amplitude $V_1$, and D and E are constants unique to each particular kind of HVPC device.

Consequently, the HVPC device 12 can detect whether a patient is properly connected to the output of the HVPC output circuit 34 and act accordingly.

Figure 6A:
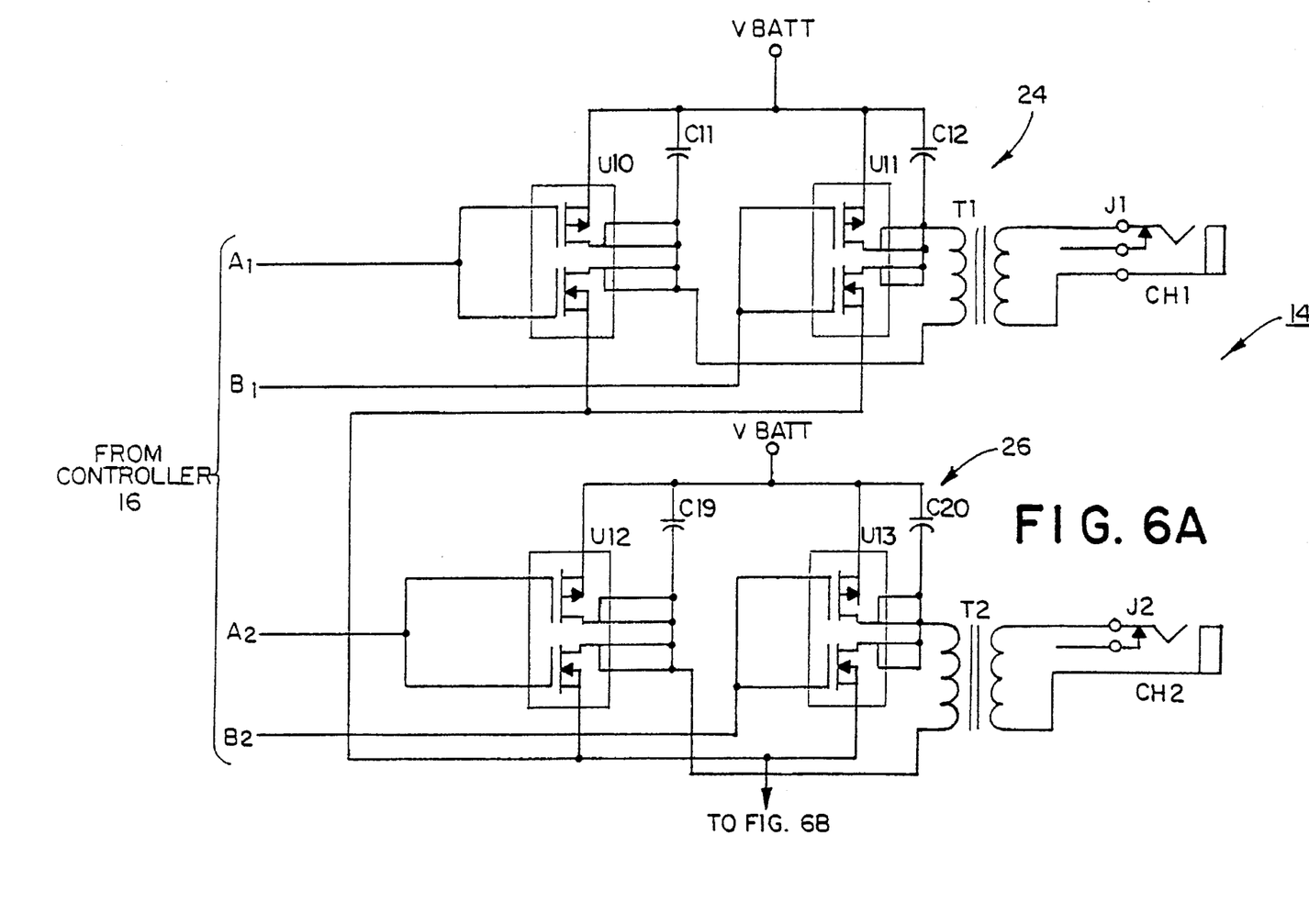
FIGS. 6A and 6B are schematic diagrams of the NMS device shown in FIG. 1, and show two NMS output circuits.
Figure 6B:
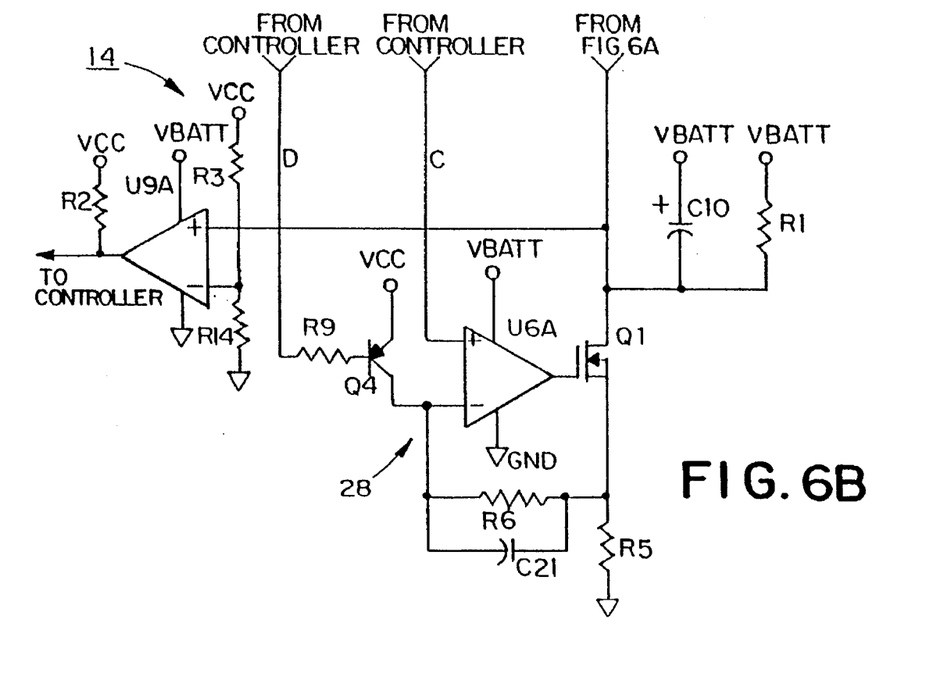

Referring now to FIGS. 6A and 6B, the NMS device 14 will now be described. As previously stated, the NMS device 14 provides constant current NMS pulses to stimulate and re-educate muscle tissue of a patient. As seen in FIG. 6A, the NMS device includes at least a first NMS output circuit 24 providing a channel 1 output and preferably a second NMS output circuit 26 providing a channel 2 output. Since the circuits 24 and 26 are identical, only circuit 24 will be described. The circuit 24 has a transformer T1 with primary and secondary coils. Devices U10 and U11 embody four transistors, each having a gate and two terminals, that combine to form an H-bridge for electrically switching current through the primary transfer coil of the transformer T1 in opposite directions for preselected periods of time. As can be seen, the current is supplied directly from the battery 22.

In order to regulate the current drawn through the primary coil of transformer T1, a constant current circuit 28 (as seen in FIG. 6B) is interconnected between both the first and second NMS output circuits 24, 26 and ground. The constant current circuit 28 includes an amplifier U6A having the output connected to the gate of a transistor Q1. Thus, the amplifier U6A controls the flow of current through transistor Q1 and through a resistor R5 to ground. The resistor R5, along with a resistor R6 and a capacitor C21, form a feedback circuit to the negative input of the amplifier U6A. A preselected reference voltage C is applied by the controller 16 to the positive input of the amplifier U6A in order to set the amount of current flow. Also, a digital signal D is applied by the controller 16 to the negative input of the amplifier U6A through a resistor R9 and a transistor Q4 in order to switch the constant current circuit 28 on and off. Of course, one skilled in the art will recognize that the constant current circuit 28 shown in FIG. 6B is only one of several equally suitable constant current circuits that may be used in the NMS device 14.

Figures 7A, 7B:
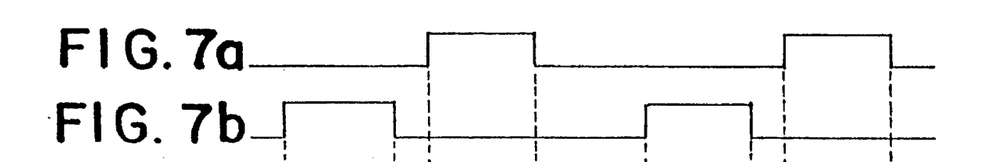
FIGS. 7a through 7d are timing diagrams showing the operation of either of the NMS output circuits of the NMS device shown in FIGS. 6A and 6B.
Figures 7C, 7D:
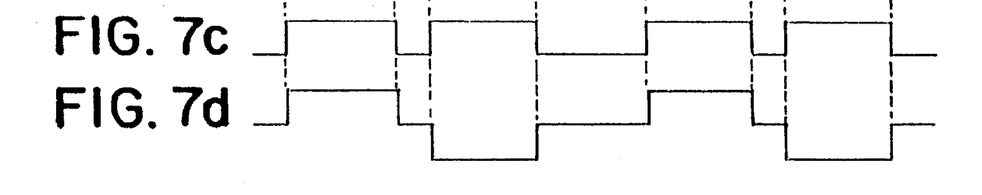

Referring now to FIGS. 7a through 7d, the operation of the first NMS output circuit 24 will be explained. FIG. 7a represents a digital signal applied by the controller 16 to device U10 through input A1 in FIG. 6A. FIG. 7b represents a digital signal applied by the controller 16 to device U11 through input B1. FIG. 7c represents a digital signal D applied by the controller 16 to operate the constant current circuit 28. FIG. 7d represents the output current at jack J1 when a patient is electrically connected to the secondary coil of the transformer T1.

As can be seen, when the controller 16 sets the voltage at input A1 to a low state, the voltage at input B1 to a high state, and the voltage D to a high state to turn on the constant current circuit 28, current flows from the battery 22 through the device U11, through the primary coil of the transformer T1 in a first direction, through the device U10, and then through the constant current circuit 28 to ground. The transformer T1 transforms the current according to the primary to secondary turns ratio, and the transformed current from the secondary coil of the transformer T1 flows in a first direction through the patient by way of electrical leads (not shown) connected to jack J1. When the controller 16 then sets voltage B1 to a low state and voltage D to a low state to turn off the constant current circuit 28, current ceases to flow.

Thereafter, when the controller sets voltage A1 to a high state, voltage B1 to a low state, and voltage D to a high state, current flows from the battery 22 through the device U10, through the primary coil of the transformer T1 in a second, reverse direction, through the device U11, and then through the constant current circuit 28 to ground. Accordingly, the transformed current flows through the secondary coil of the transformer T1 and through the patient in a second, reverse direction. When the controller 16 then sets the voltage A1 to a low state and the voltage D to a low state, current ceases to flow.

Preferably, the voltages A1, B1, and D are controlled by the controller 16 to produce the output wave form as seen in FIG. 7d. Specifically, the wave form has a positive going portion of a preselected current, a negative going portion of a preselected current, and rest portions separating the positive and negative going portions. Preferably, the preselected current of both the positive and negative-going portions is between about 1 and 100 milliamps. Preferably, the duration of the positive- and negative-portions is about 30 to about 300 microseconds. Preferably, the frequency of an NMS pulse comprising a positive- and negative-going portion is about 1 to about 100 pulses per second.

Figures 8A, 8B:
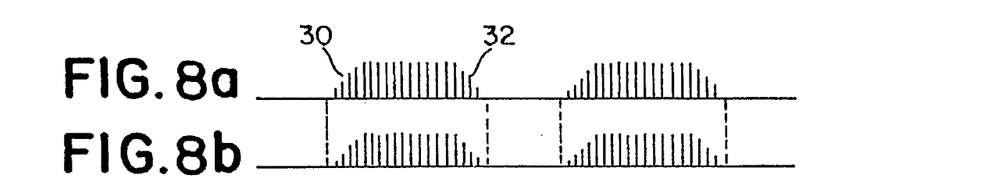
FIGS. 8a, 8b, 9a and 9b are timing diagrams showing the outputs of both output circuits in the NMS device of FIGS. 6A and 6B.
Figures 9A, 9B:
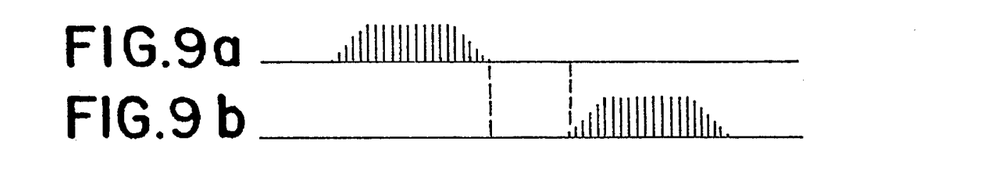

If, with respect to the NMS device 14, FIGS. 8a and 9a represent NMS pulses from the first NMS output circuit 24 and FIGS. 8b and 9b represent NMS pulses from the second NMS output circuit 26, it is seen that the NMS device 14 may be operated to provide trains of NMS pulses from both circuits 24 and 26. Further, the first and second output circuits 24 and 26 are used to provide constant current NMS pulses to first and second areas of muscular or neural tissue of the patient.

As shown in FIGS. 8a, 8b, 9a and 9b, each train of pulses may comprise a preselected ramp-up interval 30 during which the intensity of each pulse increases from a minimal value to a preselected full value. Likewise, each train of pulses may comprise a preselected ramp-down interval 32 during which the intensity of each pulse decreases from a preselected full value to a minimal value. Each train of pulses occurs for a preselected period of time, and successive trains of pulses are separated by a preselected rest interval. The first and second output circuits 24, 26 may operate simultaneously, as seen in FIGS. 8a and 8b, or alternately, as seen in FIGS. 9a and 9b.

As can be seen in FIG. 6B, the NMS device 14 also includes a patient sensor circuit comprising amplifier U9A and resistors R3 and R14 applying a predetermined voltage to the negative input of the amplifier U9A. A voltage at the drain of the transistor Q1 is applied to the positive input of the amplifier U9A. If a patient is not present during operation of the NMS device 14, current will not flow through the transformer T1. In an attempt to provide the desired current flow, amplifier U6A will turn transistor Q1 fully on, and the voltage at the positive input of amplifier U9A will be below the predetermined value set by the resistors R3 and R14. As a result, the amplifier U9A will provide a negative output to the controller 16 to signal that a patient is not attached, and the controller 16 will halt the operation of the NMS device 14.

Thus, the electrotherapy stimulator 10 of the present invention includes both an NMS device 14 providing constant current NMS pulses to muscular and neural tissue of a patient and an HVPC device 12 providing short duration low amperage high voltage constant charges to the patient. Further, the HVPC device 12 does not require a voltage regulator and can provide voltage spikes having preselected peak voltages that are not dependent upon the DC voltage of the battery 12. Additionally, the HVPC device 12 has patient detect circuitry that can disable an output circuit should a patient not be electrically connected to the output circuit.

In the foregoing description, it can be seen that the present invention comprises a new and useful electrotherapy stimulator and a method for operating the stimulator. It will be appreciated by those skilled in the art that changes could be made to the embodiments described above without departing from the broad inventive concepts thereof. It is understood, therefore, that this invention is not limited to the particular embodiment disclosed, but is intended to cover modifications within the spirit and the scope of the present invention as defined by the appended claims.

We claim:

1. An electrotherapy stimulation unit comprising a high voltage pulsed current (HVPC) electrotherapy stimulation device for providing short duration low amperage high voltage constant charge HVPC pulses to a patient to reduce pain, a neuromuscular stimulation (NMS) electrotherapy device for providing constant current NMS pulses to a patient to re-educate and prevent atrophy of muscle tissue, and a controller adapted to operate and control both the NMS electrotherapy device and the HVPC electrotherapy device.

2. The unit of claim 1 further comprising:
   controller inputs adapted to allow the patient to control the controller, the inputs including:

means to select between the operation of the NMS device and the HVPC device;

means to select an intensity for the NMS pulses and for the HVPC pulses; and a display receiving display signals from the controller, the display showing operating parameters associated with the operation of the unit during an operating mode and programming parameters associated with the programming of the unit during a programming mode.

3. The unit of claim 1 wherein the HVPC electrotherapy device comprises:

a voltage source having first and second terminals; and at least one HVPC output circuit comprising:

a coil having first and second contacts, the first contact of the coil electrically connected to the first terminal of the voltage source;

a switching device selectively electrically connecting the second contact of the coil to the second terminal of the voltage source for a preselected period of time; and a holding capacitor operatively connected to the coil, an HVPC output being operatively connected across the holding capacitor for having leads electrically connected thereto for connection to the body of the patient;

wherein when the switching device electrically connects the second contact of the coil to the second terminal of the voltage source, an increasing current is drawn through the coil, and when the switching device electrically disconnects the second contact of the coil from the second terminal of the voltage source, a voltage spike having a preselected peak voltage results across the coil and the holding capacitor is charged by the voltage spike, the charge being dissipated into the body of the patient by way of the leads.

4. The unit of claim 3 wherein the voltage source provides a variable direct current (DC) voltage, the HVPC device further comprising calculating means for calculating the preselected period of time the second contact of the coil is to be electrically connected to the second terminal of the voltage source, the preselected period of time being a function of the DC voltage and the preselected peak voltage of the voltage spike.

5. The unit of claim 4 wherein the calculating means solves the equation:

$$TIME = (V_{peak} - A)/(V_{DC} * B) + C;$$

wherein TIME is the preselected period of time, $V_{peak}$ is a value corresponding to the preselected peak voltage, $V_{DC}$ is a value corresponding to the DC voltage, and A, B, and C are predetermined constants, the predetermined constants being selected based upon the HVPC device.

6. The unit of claim 3 wherein the HVPC device provides a train of HVPC pulses, each HVPC pulse comprising first and second voltage spikes spaced by a preselected time period, each HVPC pulse in the train occurring at a preselected frequency.

7. The unit of claim 6 further comprising a patient detect circuit for detecting whether a patient is properly connected to the HVPC output of the output circuit, the patient detect circuit comprising:

means for detecting a first value corresponding to a peak amplitude of the first voltage spike in an HVPC pulse and a second value corresponding to a peak amplitude of the second voltage spike in the HVPC pulse; and means for determining a difference value corresponding to the difference between the first value and the second value, for calculating a threshold value, and for disabling the output circuit should the difference value exceed the threshold value;

whereby, when a patient is disconnected from the HVPC output of the output circuit, the holding capacitor does not fully discharge the charge from the first voltage spike before the second voltage spike recharges the holding capacitor, the second voltage spike thereby having an increased peak amplitude with respect to the first voltage spike.

8. The unit of claim 7 wherein the means for detecting the first and second values comprises a peak detect capacitor operatively connected to the coil to hold the first and second values, and wherein the controller comprises the means for determining, calculating, and disabling.

9. The unit of claim 7 wherein the threshold value is determined from the equation:

$$LIMIT = PEAK1/D + E;$$

wherein LIMIT is the threshold value, PEAK1 is the first value corresponding to the peak amplitude of the first voltage spike, and D and E are predetermined constants, the predetermined constants being selected based upon the HVPC device.

10. The unit of claim 3 wherein the coil is a primary coil, the output circuit further comprising a secondary coil inductively coupled to the primary coil to form a transformer.

* * * * *